US006150163A

United States Patent [19]

McPherson et al.

[11] Patent Number: 6,150,163

[45] Date of Patent: Nov. 21, 2000

[54] CHONDROCYTE MEDIA FORMULATIONS AND CULTURE PROCEDURES

[75] Inventors: John M. McPherson, Hopkinton; Peter C. Yaeger, Natick; Marie E. Brown, West Newton, all of Mass.; James G. Hanlon, Camarillo, Calif.; Francois Binette, Belmont, Canada

[73] Assignee: Genzyme Corporation, Cambridge, Mass.

[21] Appl. No.: 09/229,430

[22] Filed: Jan. 13, 1999

Related U.S. Application Data

[60] Provisional application No. 60/022,810, Jul. 25, 1996, provisional application No. 60/022,711, Jul. 26, 1996, and provisional application No. 60/022,801, Jul. 25, 1996.

[51] Int. Cl.[7] .............................. C12N 5/00

[52] U.S. Cl. .............................. 435/384; 435/383; 435/404; 435/405; 435/406

[58] Field of Search .............................. 435/384, 383, 435/405, 406, 404

[56] References Cited

U.S. PATENT DOCUMENTS

| | | |
|---|---|---|
| Re. 34,090 | 10/1992 | Seyedin et al. . |
| Re. 35,694 | 12/1997 | Seyedin et al. . |
| 4,774,228 | 9/1988 | Seyedin et al. . |
| 4,774,322 | 9/1988 | Seyedin et al. . |
| 4,843,063 | 6/1989 | Seyedin et al. . |
| 4,983,581 | 1/1991 | Antoniades et al. . |
| 5,118,667 | 6/1992 | Adams et al. . |
| 5,206,023 | 4/1993 | Hunziker . |
| 5,256,644 | 10/1993 | Antoniades et al. . |
| 5,270,300 | 12/1993 | Hunziker . |
| 5,328,844 | 7/1994 | Moore . |
| 5,420,243 | 5/1995 | Ogawa et al. . |
| 5,842,477 | 12/1998 | Naughton et al. . |
| 5,908,784 | 6/1999 | Johnstone et al. . |

FOREIGN PATENT DOCUMENTS

| | | |
|---|---|---|
| 0 295 605 | 6/1988 | European Pat. Off. . |
| 0 343 635 | 5/1989 | European Pat. Off. . |
| 95/00632 | 1/1995 | WIPO . |
| 96/12793 | 5/1996 | WIPO . |

OTHER PUBLICATIONS

International Search Report dated Nov. 13, 1997for corresponding PCT application PCT/US97/13140.

Adolphe, et al. "Cell Multiplication and Type II Collagen Production by Rabbit Articular Chondrocytes Cultivated in a Defined Medium," Experimental CEll Research 155: 527–536 (1984).

Jennings, Susan D. and Ham, Richard G., "Clonal Growth of Primary Cultures of Rabbit Ear Chondrocytes in a Lipid–supplemental Defined Medium," *Experimental Cell Research*, 145: 415–423 (1983).

Kato, et al., "A Serum–Free Medium Supplemented With Multiplication–Stimulating Activity (MSA) Supports Both Proliferation and Differentiation of Chondrocytes in Primary Culture," *Experimental Cell Research*, 125: 167–174 (1980).

Madsen, et al., "Growth Hormone Stimulates the Proliferation of Cultured Chondrocytes from Rabbit Ear and Rat Rib Growth Cartilage," *Nature*, 304: 545–547 (1983).

Quarto, et al., "Proliferation and Differentiation of Chondrocytes in Defined Culture Medium Effects of Systematic Factors," *Bone*, 17: 558/117 (1995).

Boumediene, et al., "Modulation of Rabbit Articular Chondrocyte (RAC) Proliferation by TGF–Beta Isoforms," *Cell Prolif.*, 28: 221–234 (1995).

Trippel, Stephen, B., "Growth Factor Actions on Articular Cartilage," *Journal of Rheumatology*, 21: 129–132 (1995).

Burton–Wurster, Nancy and Lust, George, "Fibronectin and Proteoglycan Synthesis in Long TermCultures ofCartilage Explants in Ham's F12 Supplemented witih Insulin and Calcium: Effects of the Addiction of TGF–Beta," *Archives of Biochemistry and Biophysics*, 283: 27–33 (1990).

Binette, et al., "Expression of a Stable Articular Cartilage Phenotype without Evidence of Hypertrophy by Adult Human Articular Chondrocytes In Vitro," *The Journal of Orhopaedic Research*, 16: 207–216 (1998).

Jennings, Susan, D. and Ham, Richard, G., "Clonal Growth of Primary Cultures of Human Hyaline Chondrocytes in a Defined Medium," *Cell Biology International Reports*, 7: 149–159 (1983).

Adolphe, et al., "Cell Multiplication and Type II Collagen Production by Rabbit Articular Chondrocytes Cultivated in a Defined Medium," *Experimental Cell Research*, 155: 527–536 (1984).

Yeager, et al., "Synergistic Action of Transforming Growth Factor–Beta and Insulin–like Growth Factor–Beta Induces Expression of Type II Collagen and Aggrecan Genes in Adult Human Articular Chondrocytes," *Experimental Cell Research*, 237: 318–325 (1997).

Livne, "In Vitro Response of Articular Cartilage From Magure Mice to Human Transforming Growth Factor Beta," *Acta Anat.*, 149: 185–194 (1994).

Morales, Teresa I., "Transforming Growth Factor–Beta and Insulin–like Growth Factor–1 Restore Proteoglycan Metabolism of Bovine Articular Cartilage After Depletion by Retinoic Acid," *Archives of Biochemistry and Biophysics*, 315: 190–198 (1994).

(List continued on next page.)

*Primary Examiner*—Leon B. Lankford, Jr.

[57] ABSTRACT

One object of the present invention is based upon the development and use of a serum-free defined cell culture medium comprising a supplement mixture, a component mixture, a vitamin mixture, an inorganic salt mixture and amino acid mixture that avoids the problems inherent in the use of serum. In particular, the defined medium is useful in culturing fibroblasts, especially chondrocytes. Another object of the present invention is to claim a method of enhancing the differentiation of chondrocytes and enhancing the synthesis of a cartilage specific matrix using tumor growth factor beta (TGF-β). Another object of the present invention is to claim a method of enhancing the differentiation of chondrocytes using the combination of TGF-βand IGF.

20 Claims, No Drawings

OTHER PUBLICATIONS

Tsukazaki, et al., "Effect of Tranforming Growth Factor–Beta on the Insulin–like Growth Factor–1 Autocrine/Paracrine Axis in Cultured Rat Articular Chondrocytes," *Experimental Cell Research*, 215: 9–16 (1994).

Inoue, et al., "Stimulation of Cartilage–Matrix Proteoglycan Synthesis by Morphologically Transformed Chondrocytes Grown in the Presence of Fibroblast Growth Factor and Transforming Growth Factor–Beta," *Journal of Cellular Physiology*, 138: 329–337 (1989).

Galera, et al., Effect of Tranforming Growth Factor–Beta1 (TGF–Beta1) on Matrix Synthesis by Monolayer Cultures of Rabbit Articular Chondrocytes during the Dedifferentiation Process, *Experimental Cell Research*, 200: 379–392 (1992).

Harrison, et al, "Transforming Growth Factor–Beta: Its Effect on Phenotype Reexpression by Dedifferentiated Chondrocytes on the Presence and Absence of Osteogenin," *In Vitro Cell. Dev. Biol.*, 28A: 445–448 (1992).

Luyten, et al., "Insulin–like Growth Factors Maintain Steady–State Metabolism of Proteoglycans in Bovine Articular Cartilage Explants," *Achives of Biochemistry and Biophysics*, 267: 416–425 (1988).

Sah, et al., "Differential Effects of bFGF and IGF–1 on Matrix Metabolism in Calf and Adult Bovine Cartilage Explants," *Archives of Biochemistry and Biophysics*, 308: 137–147 (1994).

Sah, et al., "Differential Effects of Serum, Insulin–like Growth Factor–I, and Firboblast Growth Factor–2 on the Maintenance of Cartilage Physical Properties During Long Term Culture," *Journal of Orthopaedic Research*, 14: 44–52 (1996).

Verbruggen, et al., "Standardization of Nutrient Media for Isolated Human Articular Chondrocytes in Gelified Agarose Suspension Culture," *Osteoarthritis and Cartilage*, 3: 249–259 (1995).

Massague, et al., "Stimulation by Insulin–like Growth Factors is Required for Cellular Transformation by Type Beta Transforming Growth Factor," *The Journal of Biological Chemistry*, 260: 4551–4554, (1985).

Rosselot, et al., "Effect of Growth Hormone, Insulin–like Growth Factor I, Basic Fibroblast Growth Factor, and Transforming Growth Factor Beta on Cell Proliferation and Proteoglycan Synthesis by Avian Postembryonic Growth Plate Chondrocytes," *Journal of Bone and Mineral Research*, 9: 431–439 (1994).

Qingqing, Gong and Pitas, Robert E., "Synertistic Effects of Growth Factors on the Regulation of Smooth Muscle Cell Scavenger Receptor Activity," *The Journal of Biological Chemistry*, 270: 21672–21678 (1995).

Frazer, et al., "Studies on Type II Collagen and Aggrecan Production in Human Articular Chondrocytes In Vitro and Effects of Transforming Growth Factor–Beta and Interleukin–1Beta," *Osteoarthritis and Cartilage*, 2: 235–245 (1994).

Galera, et al., "Transforming Growth Factor–Beta1 (TGF–Beta1) Up–Regulation of Collagen Type II Primary Cultures of Rabbit Articular Chondrocytes (RAC) Involves Increased mRNA Levels Without Affecting mRNA Stability and Procollagen Processing," *Journal of Cellular Physiology*, 153: 598–606 (1992).

Butterwith, S.C. and Goddard, C., "Regulation of DNA Synthesis in Chicken Adipocyte Precursor Cells by Insulin–Like Growth Factors, Platelet–Derived Growth Factor and Transforming Growth Factor–Beta," *Journal of Endocrinology*, 131: 203–209 (1991).

Zimber, et al., "TGF–Beta Promotes the Growth of Bovine Chondrocytes in Monolayer Culture and the Formation of Cartilage Tissue on Three–Dimensional Scaffolds," *Tissue Engineering*, 1: 289–300 (1995).

van der Kraan, et al., "Differential Effect of Transforming Growth Factor Beta on Freshly Isolated and Cultured Articular Chondrocytes," *The Journal of Rheumatology*, 19: 140–145 (1992).

Tesch, G.H., et al, "Effects of Free and Bound Insulin–Like Growth Factors on Proteoglycan Metabolism in Articular Cartilage Explants," *J. Orthop. Res.*, 10: 14–22 (1992).

Freshney, "Serum Free Media," *Culture of Animal Cells*, John Wiley & Sons, New York, 91–99 (1994).

CHONDROCYTE MEDIA FORMULATIONS AND CULTURE PROCEDURES

CROSS-REFERENCE TO RELATED APPLICATIONS

This application is related to and claims the benefit of provisional application Ser. No. 60/022,810, filed Jul. 25, 1996, provisional application Ser. No. 60/022,711, filed Jul. 26, 1996, and provisional application Ser. No. 60/022,801, filed Jul. 25, 1996.

BACKGROUND OF THE INVENTION

Initially, the successful culture of mammalian cells in vitro required supplementation of growth medium with serum which provides hormones and growth factors necessary for cell attachment and proliferation. Although serum is still widely used for mammalian cell culture, there are several problems associated with its use (Freshney, Serum-free media. In *Culture of Animal Cells*, John Wiley & Sons, New York, 91–99, 1994): 1) serum contains many unidentified or non-quantified components and therefore is not "defined"; 2) the composition of serum varies from lot to lot, making standardization difficult for experimentation or other uses of cell culture; 3) because many of these components affect cell attachment, proliferation, and differentiation, controlling these parameters, or studying the specific requirements of cells with respect to these parameters, is precluded by the use of serum; 4) some components of serum are inhibitory to the proliferation of specific cell types and to some degree may counteract its proliferative effect, resulting in sub-optimal growth; and 5) serum may contain viruses which may affect the outcome of experiments or provide a potential health hazard if the cultured cells are intended for implantation in humans.

Primarily for research purposes, there has been some effort to develop biochemically defined media (DM). DM generally includes nutrients, growth factors, hormones, attachment factors, and lipids. The precise composition must be tailored for the specific cell type for which the DM is designed. Successful growth in DM of some cell types, including fibroblasts, keratinocytes, and epithelial cells has been achieved (reviewed by Freshney,1994). However, attachment and proliferation of cells in DM is often not optimal.

One potential application of defined medium is the expansion of chondrocytes released from adult human articular cartilage for treatment of cartilage defects with autologous chondrocyte transplantation (Brittberg et al, New England Journal of Medicine, 331:889–895, 1994). Because this procedure involves the implantation of expanded chondrocytes into a patient, it may be desirable to avoid the use of serum or other undefined components during culture of the chondrocytes. For this application, the DM would need to sustain proliferation of adult human articular chondrocytes seeded at low density until confluent cultures are attained.

Several investigators have reported proliferation of high density non-articular chondrocytes in DM (Kato et al, Exp. Cell Res., 125:167–174, 1980; Madsen et al, Nature, 304:545–547, 1983; Quarto et al, Bone, 17:588, 1995). Others have reported proliferation of rabbit and human articular chondrocytes in DM (Boumedienne et al, Cell Prolif., 28:221–234, 1995; Schwartz, J. Cin. Chem. Clin. Biochem. 24:930–933, 1986). However, in these cases, chondrocytes were tested for growth in DM at high density ($\geqq$20,000 cells/cm$^2$). Jennings and Ham (Cell Biology International Reports, 7:149–159, 1983) developed a serum-free medium for proliferation of chondrocytes isolated from costal cartilage of prepubertal humans and seeded at low density. That medium required the use of polylysine-coated plates and included a liposome mixture for which the authors state that there are "inherent limitations in the degree of chemical definition".

Attempts to culture articular chondrocytes at sub-confluent densities in DM have not been successful. Adolphe et al (Exp. Cell Res., 155:527–536,1984) have developed a DM (Ham's F12 supplemented with insulin, transferrin, selenite, fibronectin, bovine serum albumin, brain growth factor, fibroblast growth factor, hydrocortisone, and multiplication stimulating activity—now known as Insulin-like growth factor II) which supports proliferation of rabbit articular chondrocytes. However, they report that serum-containing medium is necessary for the initial attachment of cells to the tissue culture vessel after seeding.

It has been reported that chondrocytes produce and secrete factors that promote their own attachment and proliferation (Shen et al, Endocrinology, 116:920–925, 1985). Examples include basic fibroblast growth factor (Hill et al, Growth Factors, 6:277–294, 1992), insulin-like growth factors (Froger-Gaillard et al, Endocrinology 124:2365–2372, 1989), transforming growth factor-β (Villiger, P.M. et al., J. Immunol., 151:3337–3344, 1993), vitronectin, and possibly some unidentified factors that promote their attachment and proliferation. Because articular cartilage is a non-vascularized tissue, and the chondrocytes embedded in cartilage have limited access to systemic growth factors, autocrine stimulation may play an important role in the maintenance and proliferative capacity of these cells. To our knowledge, autocrine stimulation of chondrocytes has not been utilized for the purpose of enhancing the proliferation of human articular chondrocytes in DM.

During expansion in monolayer in vitro, articular chondrocytes de-differentiate, decreasing synthesis of matrix molecules normally produced by differentiated articular chondrocytes. It has been shown that for cells expanded in serum-containing medium, this process can be reversed by transferring cells to a suspension culture system in the presence of serum (Benya and Shaffer, Cell, 30:215–224, 1982). If cells expanded in DM in monolayer are intended for implantation for healing of cartilage defects (Brittberg et al, 1994), it is important to demonstrate they retain the potential to redifferentiate in suspension culture. A standard procedure for testing for redifferentiation potential is to suspend cells expanded in monolayer into agarose and test for deposition of sulfated glycosaminoglycans by staining with safranin-O.

A need exists to standardize and control the proliferation and differentiation of adult human articular chondrocytes (HAC) cultured for any medical application, especially for application in humans.

SUMMARY OF THE INVENTION

One object of the present invention is based upon the development and use of a defined cell culture medium (serum-free) comprising a supplement mixture, a component mixture, a vitamin mixture, an inorganic salt mixture and amino acid mixture that avoids the problems inherent in the use of serum. In particular, the defined medium is useful in culturing fibroblasts, especially chondrocytes.

Another object of the present invention is to claim a method for enhancing the differentiation of chondrocytes and for enhancing the synthesis of a cartilage specific matrix using tumor growth factor beta (TGF-β).

Another object of the present invention is to claim a method for enhancing the differentiation of chondrocytes using a combination of TGF-β and IGF.

DETAILED DESCRIPTION OF THE INVENTION

One aspect of the present invention is based upon the development of a defined cell culture medium and culture method to standardize and control the proliferation and differentiation of human articular chondrocytes (HAC) cultured for implantation into humans for repair of articular cartilage defects.

HAC were first cultured by plating the cells at 3000 cells per $cm^2$ and allowing them to attach for one day in Dulbeccos Modified Eagles Medium (DMEM) supplemented 10% serum, then removing the serum-containing medium and refeeding with DMEM basal medium in combination with a broad array of concentrations of the supplements described in Table 1. Every two to three days thereafter, cells were refed by completely replacing DM with fresh DM. Unable to induce cells to proliferate under these conditions, different basal media were tried and found that a 1:1:1 ratio of DMEM:RPMI 1640:Ham's F12 (DRF) when combined with the supplements was effective in promoting cell proliferation after plating as above. HAC cultured in DRF+ supplements (complete DRF or cDRF) attained a terminal density equal or greater to the terminal density attained during culture in serum-supplemented medium. However, during the first several population doublings when the cell density was low, the proliferation rate was slow relative to the rate in 10% serum. We demonstrated cell proliferation without providing the cells with serum for one day prior to addition of cDRF. However, the initial growth of these cultures was slow and variable. Further experiments testing alternative supplements and different concentrations of the supplements failed to produce a cell culture system that consistently supported vigorous growth of HAC plated directly into DM without including serum at any step.

We had the idea that if we exchanged only half of the cDRF at refeeding, instead of completely exchanging the medium, factors secreted by the chondrocytes would boost their own proliferation. If the HAC secrete factor(s) required for growth in cDRF, when the cell density is sparse, the quantity of the secreted factor may be close to the threshold requirement. This would explain the slow growth in early cultures and the variable results observed in the above experiments. Using the cDRF medium combined with the approach of partial refeeding (described below), we obtained unexpectedly high yields of HAC in the complete absence of serum or any other undefined component after a brief time in culture. In the examples shown below, the volume of cDRF used was reduced relative to the volume of serum-rich medium because presumably this would increase the concentration of secreted factors in the media and further promote proliferation. Later experiments indicate that reducing the volume is not necessary and more optimal results may be achieved by using the larger volume while maintaining the practice of partial refeeding.

We have demonstrated that HAC cultured in suspension after expansion in cDRF generate colonies which stain positive with safranin-O. This indicates that, during expansion in DM, the cells have not lost their capacity to produce sulfated glycosaminoglycans, markers of chondrocyte differentiation. Because they retain their capacity to redifferentiate, chondrocytes expanded in cDRF may be suitable for autologous implantation for the purpose of healing cartilage defects.

Composition of cDRF

The culture medium, named cDRF, is composed entirely of commercially available and chemically defined basal media and growth supplements. cDRF is a modification of the DM developed by Adolphe et al (1984). As supplements to the basal media, we have discovered that insulin transferin selenium (ITS) purchased from Collaborative Biomedical Products ((CBP) Bedford, Mass.), hydrocortisone purchased from Sigma (St. Louis, Mo.), basic fibroblast growth factor (FGF), fibronectin purchased from CBP and insulin growth factor (IGF), both available from Genzyme Corporation (Cambridge, Mass.), are particularly useful in achieving the objectives of the medium described in this disclosure.

TABLE 1

| Composition of cDRF | |
|---|---|
| DMEM | 33% |
| RPMI | 33% |
| HAM'S F-12 | 33% |
| Supplements: | |
| ITS | 1% |
| Penicillin & | 100 U/ml |
| Streptomycin | 100 ug/ml |
| Hydrocortisone | 40 ng/ml |
| Basic FGF, human | 10 ng/ml |
| IGF-I, human | 1 ng/ml |
| Fibronectin, human | 5 ug/ml |

Method of preparation of cDRF

All materials are reconstituted, diluted, and stored as recommended by supplier. The three basal media, DMEM purchased from Gibco BRL, Grand Island, N.Y., Cat# 11965-084 (Table 2), RPMI DMEM purchased from Gibco BRL, Cat# 11875-051 (Table 2) and Ham's F12 purchased from Gibco BRL, Cat#11765-021 (Table 2), are combined in a 1:1:1 ratio referred to hereinafter as DRF (Table 3). ITS, penicillin/streptomycin purchased from BioWhit-taker, and hydrocortisone are diluted into DRF and this medium is stored up to 2 weeks at 2–8° C. Basic FGF, IGF, and Fibronectin are diluted into the complete DRF medium (cDRF) on the day of use for cell culture.

TABLE 2

Commercial Mediums

| | DMEM 1X Liquid mg/L | RPMI 1X Liquid mg/L | HAM'S F-12 1X Liquid mg/L |
|---|---|---|---|
| Inorganic Salts: | | | |
| $CaCl_2$ (anhyd.) | 200.00 | | 33.22 |
| $Ca(NO_3)_2.4H_2O$ | | 100.00 | |
| $CuSO_4.5H_2O$ | | | 0.0024 |
| $Fe(NO_3).9H_2O$ | 0.10 | | |
| $FeSO_4.7H_2O$ | | | 0.83 |
| KCl | 400.00 | 400.00 | 223.60 |
| $MgSO_4$ (anhyd.) | 97.67 | 48.84 | |
| $MgCl_2$ (anhyd.) | | | 57.22 |
| NaCl | 6400.00 | 6000.00 | 7599.00 |
| $NaHCO_3$ | 3700.00 | 2000.00 | 1176.00 |
| $NaH_2PO_4.H_2O^a$ | 125.00 | | |
| $Na_2HPO_4$ (anhyd.) | | 800.00 | 142.00 |
| $ZnSO_4.7H_2O$ | | | 0.86 |
| Other Components | | | |
| D-Glucose | 4500.00 | 2000.00 | 1802.00 |
| Glutathione (reduced) | | 1.00 | |
| Hypoxanthine.Na | | | 4.77 |

TABLE 2-continued

| | Commercial Mediums | | |
|---|---|---|---|
| | DMEM 1X Liquid mg/L | RPMI 1X Liquid mg/L | HAM'S F-12 1X Liquid mg/L |
| Linoleic Acid | | | 0.084 |
| Lipoic Acid | | | 0.21 |
| Phenol Red | 15.00 | 5.00 | 1.20 |
| Putrescine 2HCl | | | 0.161 |
| Sodium Pyruvate | | | 110.00 |
| Thymidine | | | 0.70 |
| Amino Acids: | | | |
| L-Alanine | | | 8.90 |
| L-Arginine | | 200.00 | |
| L-Arginine.HCl | 84.00 | | 211.00 |
| L-Asparagine.$H_2O$ | | | 15.01 |
| L-Asparagine (free base) | | 50.00 | |
| L-Aspartic Acid | | 20.00 | 13.30 |
| L-Cystine.2HCl | 63.00 | 65.00 | |
| L-CysteineHCl.$H_2O$ | | | 35.12 |
| L-Glutamic Acid | | 20.00 | 14.70 |
| L-Glutamine | 584.00 | 300.00 | 146.00 |
| Glycine | 30.00 | 10.00 | 7.50 |
| L-Histidine.HCl.$H_2O$ | 42.00 | | 21.00 |
| L-Histidine (free base) | | 15.00 | |
| L-Hydroxyproline | | 20.00 | |
| L-Isoleucine | 105.00 | 50.00 | 4.00 |
| L-Leucine | 105.00 | 50.00 | 13.10 |
| L-Lysine.HCl | 146.00 | 40.00 | 36.50 |
| L-Methionine | 30.00 | 15.00 | 4.50 |
| L-Phenylalanine | 66.00 | 15.00 | 5.00 |
| L-Proline | | 20.00 | 34.50 |
| L-Serine | 42.00 | 30.00 | 10.50 |
| L-Threonine | 95.00 | 20.00 | 11.90 |
| L-Tryptophan | 16.00 | 5.00 | 2.00 |
| L-Tyrosine.2Na.$2H_2O$ | 104.00 | 29.00 | 7.81 |
| L-Valine | 94.00 | 20.00 | 11.70 |
| Vitamins: | | | |
| Biotin | | 0.20 | 0.0073 |
| D-Ca pantothenate | 4.00 | 0.25 | .50 |
| Choline Chloride | 4.00 | 3.00 | 14.00 |
| Folic Acid | 4.00 | 1.00 | 1.30 |
| i-Inositol | 7.20 | 35.00 | 18.00 |
| Niacinamide | 4.00 | 1.00 | 0.036 |
| Para-aminobenzoic Acid | | 1.00 | |
| Pyridoxine HCL | | 1.00 | 0.06 |
| Pyridoxal HCl | 4.00 | | |
| Riboflavin | 0.40 | 0.20 | 0.037 |
| Thiamine HCl | 4.00 | 1.00 | 0.30 |
| Vitamin $B_{12}$ | | 0.005 | 1.40 |

TABLE 3

| DRF | |
|---|---|
| Inorganic Salts: | |
| $CaCl_2$ (anhyd.) | 233.22 |
| $Ca(NO_3)_2.4H_2O$ | 100.00 |
| $CuSO_4.5H_2O$ | 0.0024 |
| $Fe(NO_3).9H_2O$ | 0.10 |
| $FeSO_4.7H_2O$ | 0.83 |
| KCl | 1023.60 |
| $MgSO_4$ (anhyd.) | 146.51 |
| $MgCl_2$ (anhyd.) | 57.22 |
| NaCl | 19999.00 |
| $NaHCO_3$ | 6876.00 |
| $NaH_2PO_4.H_2O^a$ | 125.00 |
| $Na_2HPO_4$ (anhyd.) | 942.00 |
| $ZnSO_4.7H_2O$ | 0.86 |
| Other Components | |
| D-Glucose | 8302.00 |

TABLE 3-continued

| DRF | |
|---|---|
| Glutathione (reduced) | 1.00 |
| Hypoxanthine.Na | 4.77 |
| Linoleic Acid | 0.084 |
| Lipoic Acid | 0.21 |
| Phenol Red | 21.20 |
| Putrescine 2HCl | 0.161 |
| Sodium Pyruvate | 110.00 |
| Thymidine | 0.70 |
| Amino Acids: | |
| L-Alanine | 8.90 |
| L-Arginine | 200.00 |
| L-Arginine.HCl | 295.00 |
| L-Asparagine.$H_2O$ | 15.01 |
| L-Asparagine (free base) | 50.00 |
| L-Aspartic Acid | 33.30 |
| L-Cystine.2HCl | 128.00 |
| L-Cysteine HCl.$H_2O$ | 35.12 |
| L-Glutamic Acid | 34.70 |
| L-Glutamine | 1030.00 |
| Glycine | 47.50 |
| L-Histidine.HCl.$H_2O$ | 63.00 |
| L-Histidine (free base) | 15.00 |
| L-Hydroxyproline | 20.00 |
| L-Isoleucine | 159.00 |
| L-Leucine | 168.10 |
| L-Lysine.HCl | 222.50 |
| L-Methionine | 49.50 |
| L-Phenylalanine | 86.00 |
| L-Proline | 54.50 |
| L-Serine | 82.50 |
| L-Threonine | 126.90 |
| L-Tryptophan | 23.00 |
| L-Tyrosine.2Na.$2H_2O$ | 140.81 |
| L-Valine | 125.70 |
| Vitamins: | |
| Biotin | .2073 |
| D-Ca pantothenate | 4.75 |
| Choline Chloride | 21.00 |
| Folic Acid | 6.30 |
| i-Inositol | 60.20 |
| Niacinamide | 5.036 |
| Para-aminobenzoic Acid | 1.00 |
| Pyridoxine HCL | 1.06 |
| Pyridoxal HCl | 4.00 |
| Riboflavin | 0.637 |
| Thiamine HCl | 5.30 |
| Vitamin $B_{12}$ | 1.405 |

Articular cartilage was harvested from femoral condyles of recently deceased human donors (age range: 29 to 53) within 24 hours of death and stored in isotonic media for up to 4 days at 2–8° C. Chondrocytes (HAC) were released from the cartilage by overnight digestion in 0.1% collagenase/DMEM. Remaining cartilage was further digested for 4 hours in 0.1% collagenase/0.25% trypsin/DMEM. The released cells were expanded as primaries in DMEM supplemented with 10% Fetal Bovine Serum, 100 U/ml Penicillin, and 100 ug/ml Streptomycin (serum-rich medium). At near confluence, cells were frozen in 10%DMSO/40% serum/50%DMEM.

For experiments performed with 2nd passage cells, ampules of frozen primaries were thawed, rinsed in media indicated below for initial seeding. For experiments performed in 3rd passage, cells were expanded through 2nd passage in serum-rich media, harvested by trypsinization, and washed in seeding media as indicated.

The following disclosure describes the use of collagen matrices and the cytokine TGF-β to enhance the redifferentiation and cartilage matrix formation process for dedifferentiated human articular chondrocytes. These findings are novel in that the application demonstrates how the cytokine augments the re-expression of the differentiated chondrocyte phenotype for passaged and dedifferentiated human cells in a matrix rather than simply supporting the differentiated phenotype for chondrocytes freshly released from cartilage tissue (primary cells) as others have shown (1,2). For those that have looked at the cytokine and its effect on re-expression, none have used it in a collagen matrix. The re-expression work centered on either rabbit cells in an agarose matrix (3,4) or else the factors effect on human chondrocyte proliferation (5) and not differentiation specifically. This disclosure is a first demonstration that the use of the cytokine can augment the redifferentation of the cells and enhance the rate at which new cartilage specific matrix is synthesized in the collagen sponge environment. This should enhance the ability of this system to regenerate new tissue, support increased mechanical loads and reform the articular surface.

This disclosure describes a completely defined medium which will permit the re-expression of CII, a marker for chondrocyte differentiation, in a suspension of normal adult human articular chondrocytes that have de-differentiated as a consequence of expansion in monolayer in vitro. It has been discovered that TGF-β1 or β2 and IGF-I satisfy the growth factor requirement for this differentiation process. This combination of growth factors in defined medium is potentially applicable to improvements in the procedure of chondrocyte autologous transplantation (Bittberg et al, 1994). It may be used to prime chondrocytes for differentiation prior to implantation. Alternatively, it may be included as a supplement at the time of implantation of the chondrocytes. This growth factor combination may also be used as a differentiation-stimulating supplement to chondrocytes embedded in a matrix intended for implantation into cartilage defects.

EXAMPLE 1

To test the concept of partial refeeding with cDRF, we compared chondrocyte growth by this new method with growth in culture conditions which we were familiar with: culture in Fetal Bovine Serum (FBS) or culture in cDRF after one day in FBS with complete refeeding. Human chondrocytes from a 31 year old donor (HC31 cells) at 3rd passage were cultured under the conditions 1,2 & 3 described below.

Culture Condition 1 (FBS/complete refeeding)

Chondrocytes prepared as described above were seeded in triplicate into 10 $cm^2$ tissue culture wells at a density of 3,000 cells per $cm^2$ in 5 ml 10% FBS/DMEM and refed with 5 ml 10% FBS/DMEM one day after seeding and every 2–3 days thereafter. At each refeeding, all media was removed and replaced with 5 ml of fresh medium.

Culture Condition 2 (FBScDRF/complete refeeding)

Chondrocytes were cultured as for condition 1 except that after one day in 10% FBS/DMEM, all refeedings were done with cDRF.

Culture Condition 3 (FBS-cDRF/partial refeeding)

Chondrocytes were cultured as for condition 1, except that after one day in 10% FBS/DMEM, all medium was removed and replaced with 3 ml cDRF. At each refeeding thereafter, partial refeeding was achieved by removing 1.5 ml of used cDRF and replacing with 1.5 ml of fresh cDRF.

Cells were harvested at 7 and 13 days after seeding and samples were counted on a hemacytometer. The results in Table 4 show a marked enhancement of cell yield at 7 days and at 13 days in conditions of partial refeeding with cDRF compared to that of complete refeeding.

TABLE 4

Example 1 results

| Exp 1 Culture conditions | | | Strain HC31, 3rd passage Cell density at harvest (1000's of cells/$cm^2$ +/− sem) | |
|---|---|---|---|---|
| # | Day 0–1 | Days 2–13 | Day 7 | Day 13 |
| 1 | 10% FBS | 10% FBS Complete refeed | 77 +/− 7 | 109 +/− 10 |
| 2 | 10% FBS | cDRF Complete refeed | 29 +/− 1 | 72 +/− 13 |
| 3 | 10% FBS | cDRF Partial refeed | 103 +/− 9 | 157 +/− 7 |

EXAMPLE 2

We repeated example 1 but added in one more condition to determine whether we could eliminate the use of serum during the first day after seeding:

Culture Condition 4 (cDRF/partial refeeding)

Chondrocytes were cultured as for condition 1, except that they were seeded in 3 ml cDRF instead of 5 ml serum-rich media. At each refeeding, 1.5 ml of used cDRF was replaced with 1.5 ml of fresh cDRF.

Cells were harvested at 7 days after seeding. The results in Table 5 are generally similar to the results of example 1 for the three culture conditions that were repeated. Interestingly, the additional culture condition, in which direct plating of cells into cDRF was combined with partial refeeding, yielded a yet higher quantity of cells.

TABLE 5

Example 2 results

| Ex 2 Culture conditions | | | Strain HC31, 3rd passage |
|---|---|---|---|
| # | Day 0–1 | Days 2–7 | Cell density at Day 7 (1000's of cells/$cm^2$ +/− sem) |
| 1 | 10% FBS | 10% FBS Complete refeed | 82 +/− 4 |
| 2 | 10% FBS | cDRF Complete refeed | 29 +/− 3 |
| 3 | 10% FBS | cDRF Partial refeed | 73 +/− 2 |
| 4 | cDRF | cDRF Partial refeed | 126 +/− 2 |

EXAMPLE 3

We repeated example 2 with three additional human articular chondrocyte strains. The results in Table 6 show that partial refeeding consistently and substantially outperforms complete refeeding (condition 3 vs 2). Unexpectedly, plating directly into defined medium consistently outperforms attachment in serum, when partial refeeding is done in both cases (condition 4 vs 3). With the exception of one strain, partial refeeeding with defined medium outperforms culture in 10% FBS with complete refeeding.

TABLE 6

Example 3 results

| Exp 3 Culture conditions | | | 2nd passage, Cell density at Day 7 (1000's of cells/$cm^2$ +/− sem) | | | |
|---|---|---|---|---|---|---|
| # | Day 0–1 | Days 2–7 | Strain HC31 | Strain HC53 | Strain HC29 | Strain HC34 |
| 1 | 10% FBS | 10% FBS Complete refeed | 88 +/− 4 | 69 +/− 5 | 75 +/− 7 | 53 +/− 3 |
| 2 | 10% FBS | cDRF Complete refeed | 24 +/− 3 | 40 +/− 1 | 9 +/− 3 | 6 +/− 0 |
| 3 | 10% FBS | cDRF Partial refeed | 60 +/− 3 | 81 +/− 9 | 40 +/− 7 | 10 +/− 1 |
| 4 | cDRF | cDRF Partial refeed | 202 +/− 5 | not done | 88 +/− 4 | 27 +/− 4 |

Although there are only results for the 7 day timepoint in examples 2 & 3, the three examples combined are a strong indication that we can consistently attain cell densities of >100,000 cells/$cm^2$within two weeks of culture by thawing frozen 1st passage cells, plating directly into defined medium without serum, and refeeding with half volumes.

EXAMPLE 4

We repeated example 2 again. In addition, we added one other condition to determine whether the partial refeeding method conferred an advantage to chondrocytes cultured in FBS:

Culture Condition 5 (FBS/partial refeeding)

Chondrocytes were cultured as for condition 1 except that at each refeeding, half the media was removed and replaced with fresh media.

The results in Table 7 are again consistent with previous examples showing a clear advantage of partial refeeding over complete refeeding when cDRF medium is used. In contrast, when serum-rich media is used, the partial refeeding method does not increase and may decrease cell yields.

TABLE 7

Example 4 results

| Ex 4 Culture conditions | | | Strain HC31, 2nd passage Cell density at Day 7 |
|---|---|---|---|
| # | Day 0–1 | Days 2–7 | (1000's of cells/$cm^2$ +/− sem) |
| 1 | 10% FBS | 10% FBS Complete refeed | 77 +/− 2 |
| 2 | 10% FBS | cDRF Complete refeed | 26 +/− 5 |
| 3 | 10% FBS | cDRF Partial refeed | 67 +/− 11 |
| 4 | cDRF | cDRF Partial refeed | 103 +/− 3 |
| 5 | 10% FBS | 10% FBS Partial refeed | 49 +/− 2 |

EXAMPLE 5

To assess the redifferentiation potential of chondrocytes after their expansion in monolayer culture in cDRF by the partial refeeding method, their capacity to form colonies in agarose which bind safranin-O (Saf-O positive colonies) was assessed. Strain HC31 chondrocytes prepared as described above were thawed and seeded at 2nd passage into 225 $cm^2$ tissue culture flasks (T225) at a density of 2,200 cells per $cm^2$ in 100 ml cDRF per T225. Cells in cDRF were refed by removing 50 ml (one-half the total volume) and replacing with 50 ml fresh cDRF. Refeeding was done one day after plating and every 2–3 days thereafter. As a positive control, parallel cultures were plated in 60 ml 10% FBS/DMEM per T225. Cells in 10% FBS/DMEM were refed by removing the full volume of used medium and replacing with 60 ml fresh 10% FBS/DMEM. Four T225s were plated for each condition.

Cells were harvested by trypsinization from two T225's per culture condition at 12 and 14 days after seeding. At harvest, the cells were suspended at $2.5\times10^5$ cells per ml in 10% FBS/DMEM and mixed 1:1 with 4% low-melt agarose. Four ml of the cell/agarose suspension were plated onto a layer of 2 ml solidified high-melt agarose in 60 mm tissue culture dishes (P60). Platings were done in duplicate or triplicate. After solidification, the cultures were overlaid with 5 ml 10% FBS/DMEM. The cultures were refed after 2–3 hours of equilibration and every 2–3 days thereafter until fixation.

After 3 weeks in agarose culture, the cells were fixed in 10% formalin and stained with safranin-O. Saf-O positive colonies of ≧2 $\mu$m diameter were counted using a microscope. For each corresponding monolayer condition, a total of 10 grids of 4 $mm^2$ each were counted randomly from 2 P60s.

The results in Table 8 show that the capacity of HAC expanded in cDRF to generate Safranin-O colonies after suspension in agarose is not statistically different than that of cells expanded in FBS. The similarity is clearer in the results from the 14 day monolayer cultures which have a smaller sampling error. The reduction in the number of colonies generated after 14 days in monolayer, either FBS or cDRF, may be the consequence of maintaining the cells in monolayer in a post-confluent state.

TABLE 8

Differentiation of HAC in agarose after expansion in cDRF or FBS

| Days in monolayer | Growth medium | # of safranin-O colonies ≧ 2 um per 10 grids (40 $mm^2$) 3 weeks after suspension in agarose (average of two cultures +/− s.e.m.) |
|---|---|---|
| 12 | 10% FBS | 436 +/− 31 |
| | cDRF, partial refeed | 327 +/− 96 |
| 14 | 10% FBS | 203 +/− 38 |
| | cDRF, partial refeed | 249 +/− 20 |

EXAMPLE 6

Primary chondrocytes were isolated from cartilage tissue from the femoral head of a 31 year old male. The cells were subcultured in monolayer. At third passage, the cells were seeded into a type-I collagen sponge matrix (Instat, Johnson&Johnson) at $10^7$ cells/ml and cultured in DME media supplemented with either 10% fetal bovine serum (serum control), 1% ITS+media supplement (serum free control) or ITS+with TGF-β1 at 1 or 5 ng/ml ("low dose" or "high dose", Collaborative Biomedical Products, Bedford, Mass.). The DME media is standardly available, and may preferably include high glucose without sodium pyruvate. Differentiation state of the cells was determined by gene expression analysis with RNase protection (Hybspeed RPA Kit, Austin Tex.) using 32P-labeled mRNA probes for type-I and type-II collagen and the cartilage specific proteoglycan Aggrecan. Matrix deposition was studied by use safranin-O/fast green stain as well monoclonal antibody staining for collagen type-II and chondroitin sulfate. mRNA analysis of monolayer cells demonstrates type-I collagen expression with trace type-II and Aggrecan expression for the chondrocytes at the time of seeding. Upregulation of type-II collagen with concurrent downregulation of type-I collagen expression was consistently observed for samples cultured in high dose TGF-β supplemented and serum control cultures. In serum free and low dose TGF-β conditions only modest type-I collagen downregulation is observed. This concurrent expression behavior for type-I and type-II collagens is consistent with re-expression of the differentiated chondrocyte phenotype. By 4-weeks, an enhanced level of re-differentiation as shown by RNase protection, was observed for samples cultured in high dose TGF-β culture over the other groups. 8-weeks there was extensive proteoglycan staining throughout the thickness of the matrix for samples cultured in high dose TGF-β conditions demonstrated by both immuno- and histologic staining. For low dose TGF-β and for serum and serum free controls, new matrix staining was relegated to the periphery or isolated pockets within the sponge matrix. This study demonstrates that passaged human chondrocytes can re-express their differentiated phenotype in the type-I collagen sponge environment. The level of re-differentiation was demonstrated both at the genetic expression and at the matrix deposition level. TGF-β modulated this process by enhancing the rate of redifferentiation and the amount of new matrix deposition.

EXAMPLE 7

Confluent or near-confluent third passage adult human femoral condyle chondrocytes were harvested by trypsinization and suspended in alginate beads at a density of $10^6$ cells/ml. For each example described below, cells in alginate were cultured at 37° C., 9% $CO_2$, in 25 mM HEPES buffered DMEM supplemented with 100U/ml penicillin, 100 $\mu$g/ml streptomycin (basal medium), and additional supplements as indicated. Storage and dilution of supplements were performed as recommended by suppliers. For each culture, 8 ml of alginate beads (8 million cells) were incubated in a 150 $cm^2$ flask in 40 ml of the indicated media. Cultures were re-fed every 2–3 days. At timepoints indicated, cells were released from alginate, pelleted, frozen and stored. RNA was isolated from the cell pellets and quantitated. The effect of the different culture conditions on the abundance of for collagen type I (CI) , collagen type II (CII), aggrecan (Agg) mRNAs was determined by the Rnase protection assay, using 18 S rRNA (18 S) detection as an internal standard. The RNA probes used in the Rnase protection assay were transcribed from templates containing cDNA segments of the human genes for CI, CII, Agg, and 18 S. The culturing of cells in alginate was done according to Guo, et al., Connective Tissue Research, 19: 277–297, 1989. The isolation of RNA was done according to manufacturer's instructions using the Qiashredder™ and RNeasy™ kits purchased from Qiagen (Chatworth, Calif.). Rnase Protection assays were performed according to manufacturers instructions using Hybspeed™ RPA kit purchased from Ambion (Austin, Tex.).

Alginate culture and RNase protection assay protocols

OUTLINE

I. Expansion of chondrocytes in monolayer (1–2 weeks)

II. Culture of chondrocytes in alginate (1 week–6months)

A. Inoculation of cells into alginate beads

B. Refeeding

C. Harvesting cells from alginate beads

STOP POINT

III. Isolation, quantitation and aliquoting of cellular RNA (1–2 days; 1 day per set of RNA preps)

A. Isolation

B. Quantitation

C. Aliquoting

STOP POINT

D. Visualization of RNA samples on agarose gels (evaluation of RNA degradation)

STOP POINT

IV. RNase protection assays (1–5 days)

A. Preparation of specific cDNA templates with T7 promoter in antisense orientation (performed by FB)

Day 1

B. In vitro transcription from cDNA to prepare antisense radioactive RNA probes from cDNAs, followed by Dnase treatment to remove cDNA template (should be done within 3 days of Hybrization step, preferably the day before)

C. Gel purification of radioactive probes

D. Co-precipitation of cellular RNA with antisense probes (should be done the day before Hybrization step)

Day 2

E. Hybrization of cellular RNA with antisense probes and RNase treatment to remove ssRNA F. Electophoresis of protected RNA G. Quantitation on phosphimager For R& D studies of chondrocyte differentiation, we cultured chondrocytes in alginate beads followed by detection of chondrospecific gene expression using RNase protection assays. The procedures, written in detail below, are derived from the following sources;

Alginate culture: Guo et al (1989) Connective Tissue Research 19:277–297

RNA isolation: Handbook from RNeasy Total RNA Kit (Qiagen, Cat # 74104)

In Vitro Transcription: Instruction Manual from MAXI-script T7 In Vitro Transcription Kit (Ambion, Cat # 1314)

RNase Protection Assay: Instruction Manual from Hyb-Speed RPA kit (Ambion,Cat # 1412)

DETAILED PROTOCOLS

I. Culture of chondrocytes in alginate (1 week–6 months)

A. Inoculation of cells into alginate beads

Materials

Monolayer cultures of chondrocytes, >8 million cells per 8 ml alginate culture to be inoculated PBS, 20 mt/T150

Trypsin/EDTA (T/E), 20 ml per T150

DMEM 10% FBS for washing trypsinized cells, 30 ml per T150

0.15 M NaCl/25 mM HEPES, pH 7.4 (Isotonic Salt Solution),

~30 ml per T150 flask of monolayer cells+~200 ml per 8 ml alginate culture 1.2% alginate/0.15% NACl/25 mM HEPES, pH 7.4,warmed to RT, 8 ml per alginate culture Recipe (per 100 ml):

Position a glass beaker containing 100 ml Isotonic Salt Solution under a Polytron mixer. Insert the end of the Polytron in the solution and run at high speed while very slowly adding 1.2 grams of alginate (Improved Kelmar, from Kelco) and moving the beaker. After the alginate appears to be complete dissolved (~10–15 minutes), add magnetic stirbar and stir for ~30 minutes. Autoclave 30 minutes, then run through 0.45 micron filter then 0.22 micron filter and store for up to six months in the refrigerator.

0.1 M $CaCl_2$/25 mM HEPES, pH 7.4, 80 ml per 8 ml alginate culture

Medium for culture of chondrocytes in alginate, 40 ml per 8 ml alginate culture

Note: the basal medium affects the stability of the alginate beads; if using something other than DME as basal media, preliminary tests need to be done to test bead stability. See Guo et al (1989) Connective Tissue Res. 9:277

22 gauge needles and 10 ml syringes, one per alginate culture 25 mM HEPES -buffered DMEM, 120 ml per 8 ml alginate culture T75 tissue culture flasks, one per alginate culture Plastic bottle for suspension of cells in NaCl, one for each set of alginate cultures, maximum of 6 alginate cultures per set (capacity of ~50–60 ml per monolayer T150 culture).

125 ml bottles, 1 per alginate culture 70 micron filters, 1 per alginate culture Procedures To avoid prolonged exposure of cells to 0.1 M Ca $Cl_2$, prepare only ~6 alginate cultures (~48 million cells) at one time from monolayer culture 1)Prepare all materials listed above and prewarm EXXXX and growth media 2)warm T/E, 20 ml per T150 to be harvested 3)Aspirate media from each T150 monolayer flask, add 20 ml PBS to each, and aspirate 4)Add 20 ml T/E per T150, incubate ~2 minutes, suspend cells, rinse bottom of flask with 30 ml DMEM 10%FBS 5)Transfer to conical tube, pellet cells, resuspend each in 25 ml Isotonic Salt Solution, and combine into one plastic bottle 6) Rise the empty tubes in series with 30 ml Isotonic Salt Solution and add to cell suspension Note total volume of cell suspension 7)Take ~1 ml sample of cells to count on hemacytometer and fill four hemacytometer wells 8)RECORD cell yield and density of monolayer cultures at time of harvest 9)distribute 8 million cells into each 50 ml conical tubes (one per alginate culture or timepoint( and pellet 8 minutes at 1000 rpm 10)From one tube, aspirate sup, label T=0, immerse in liquid nitrogen, and freeze cell pellet immediately at −80° C. (for RNA sample of monolayer culture)

11)add 8 ml 1.2% alginate solution to each remaining cell pellet and resuspend by pipetting up and down about 30 times (do not introduce air bubbles.)

12) For each cell/alginate suspensions:

(i) mix again by pipetting up and down five times and transfer the suspension into a 10 ml syringe fitted with a 22 gauge needle, using a 10 ml pipette.

(ii) cover with plunger, invert, and remove air by depressing plunger and tapping to remove bubbles (iii) cover with plunger, invert, and remove air by depressing plunger and tapping to remove bubbles (iv) allow alginate beads to cure for 5–15 minutes at RT, no longer than this.

(v) pour $CaCl_2$ through 70 $\mu$m filter into waste bucket, and wash 2× with 100 ml Isotonic Salt Solution, and 2X with 60 ml DMEM using 70 $\mu$m filter and waste bucket 13) Resuspend each tube of beads into 20 ml of respective media and transfer to labelled T162, then rinse remaining beads into flask with another 20 ml. (~8 million cells per T162, or somewhat less as ~1 ml is lost during transfer into syringe)

14) place loosely capped flasks in incubator.

B. Refeeding, every 2–3 days

For each alginate culture:

1) Stand flask on end, and tilt to allow beads to settle in one corner of flask.

2) With 50 ml pipet, remove media from above the beads (~25–30 ml)

3) Place 50 ml pipette tightly against bottom end of the flask, and slowly lay flask flat on its end.

4)Withdraw all media from flask into pipet, maintaining contact between pipet tip and bottom of flask to avoid drawing beads into pipet.

5) Lift pipet above surface of media and examine for beads settling to tip of pipet. Dispel any beads that may be settled in pipet tip.

6) Discard media into bucket

7) Add 40 ml fresh prewarmed media to beads

8) Repeat for next culture. USE SEPARATE PIPET FOR EACH CULTURE

C. Harvesting cells from alginate beads and:

i) determine cell yields ii) snap freeze cell pellets for RNase protection assay iii) prepare cytospin slides for antibody staining Materials, quantity per alginate culture labelled 50 ml conical tubes, I 50 ml pipettes, 1

70 micron-pore filters, 1

0.15 M Na Cl/25 mM HEPES, p H 7.4–175 ml 55 mM Na Citrate/100 mM Na Cl/25 mM HEPES<p H 7.4~45 ml microfuge tubes for samples for counting (labelled for each culture), 1

Trypsin/EDTA std working solution, 100 $\mu$l hemacytometers, 1 labelled 15 ml tubes for cytospin aliquots, 1 cytospin loading and slide assembly, labelled ≧6

4% paraformaldehye, 200 ml (use within one week, store tightly capped at 4° C.)

Note: paraformaldehye is toxic

To prepare 200 ml:

i)in fume hood, warm 200 ml PBS+200 $\mu$l 2N Na OH to 70–75° C. on hot stir plate; do not heat above 80° C.

ii) Turn off heat, add 8 g paraformaldehyde and stir with magnetic stir bar until solution becomes clear (less than one hour) Be sure to clean up any paraformaldehyde dust.

iii) test pH; pH should be between 7 & 7.5 iv) filter through Whatman paper #1 in fume hood

70% EtOH, 200 ml

PBS, 200 ml

Holders for submerging cytospin slides

Holders for storing cytospin slides

Methods 1) photograph beads under microscope 2) transfer cells of each flask to separate 50 ml conical tube, using 30 ml pipets 3) wash 3×_WITH 0.15 m nAcL/25 Mm HEPES i)Drain liquid into waste bucket using 70 micron filter ii)Add 0.15M NaCl/25 mM HEPES to 45 ml mark on conical tube by pouring iii) Repeat draining and pouring 2 more times, and drain once more.

4)add 55 mM NaCitrate/100 mM NaCl/25 mM HEPES to 50 ml mark and repeatedly invert gently for 5–8 minutes (for ~one minute after beads become undetectable by eye).

5) centrifuge 8 min at 1000 rpm in tabletop IEC (or Mistral) centrifuge 6) aspirate sup and resuspend in 20 ml 0.15 M NaCl/25 m M HEPES.

7) mix well, transfer 100 μl into microfuge tube containing 100 μl T/E for counting (step 11) and place tubes in 37° C. water bath 8) count cells (from step 7, two hemacytometer wells/sample)—cell samples from cultures not to be put on cytospin can be counted after last step

RECORD CELL COUNTS cell yield per culture+(counts/5 fields)

$(20)(2)(10^4)/5$=(counts/5 fields)(80,000)

9) aliquot cells from each culture into 15 ml tubes for cytospin, enough for 50,000 cells per slide, at least six slides per culture 10) add 30 ml 0.15 M Na Cl/25 mM HEPES to step 6 suspension 11) centrifugation at 1000 rpm for 8 minutes 12) aspirate sup and IMMEDIATELY freeze cell pellet at −80° C.

Ideally, it is better to snap-freeze cells in liquid nitrogen or dry ice/ethanol bath, and then move to −80° C. for storage. Slow freezing may lead to degradation of cellular RNA 13) dilute aliquots of cells for cytospin to 50,000 cells/500 μl 14) load 500 μl sample (50,000 cells) into each cytospin loading device (at least six samples per cell culture)

15) Spin cyospin devices at 800 rpm for 5 minutes (Program #1)

16) Air dry for 1–2 minutes in tissue culture hood

17) Fix in 4% paraformaldehyde for 5 minutes

18) Drain slides and transfer to PBS for 2 minus

19) Drain slides and transfer to 70% EtOH for 3 minutes

20) Air dry in hood for 15 minutes or until completely dry.

21) Store at −80° C. Upon thawing, fix in 4% formaldehyde for 2 min and rinse with PBS.

STOP POINT: RNA within cell pellet stored at −80° C. should be stable "indefinitely"

III. Isolation, quantitation, aliquoting, and get electrophoresis of cellar RNA (1–2 days; 1 day per set of RNA preps)

Materials for isolation, quantitating, and aliquoting quantity per RNA prep

Gloves

Autoclaved, labelled microfuge tubes, 1

RNeasy Total RNA Kit, Qiagen

Lysis buffer RLT: 600 μl 2 ml collection tubes, labelled:1 spin columns in 2 ml collection tubes, 1

Wash buffer RW1: 700 μl

Wash buffer RPE concentrate: 200 μl (or 1 ml if already diluted with ethanol)

1.5 ml collection tubes, labelled: 1

Beta mercaptoethanol (BME), 6 μl

QIA shredder in 2 ml collection tube (Qiagen), 1 units

70% ethanol/30% DEPC-treated $H_2O$, 600 μl

100% Ethanol, 800 μl (for diluting RPE concentrate, unless RPE is already diluted)

DEPC -treated $dH_20$/0.1 mM EDTA, 50–200 μl (depending on yield of RNA)

Rnase-free pipet tips with aerosol barrier for P2, P20, P200 and P1000

650 μl presiliconized, Rnase-free microfuge tubes (Sorenson), 5

Screw-cap microfuge tubes for storage: 1

Spectrophotometer and UV Silica Ultra Microcell (Beckman Cat# 514261)

Capillary UV "cuvettes", 0.5 mm pathlength (Beckman Cat# 514262)

Procedures

A. Isolation

1) Review notes p7 of RNeasy handbook (attached); This includes important notes regarding prevention of RNA degradation, handling of kit components, and limitations of the RNeasy kit 2) Label tubes/columns for tracking of RNA samples throughout procedure; 1.5 ml autoclaved microfuge tubes for initial transfer of cells/lysis buffer suspension, 1 per RNA sample QIA shredder columns in 2 ml collection tubes, 1 per RNA sample RNeasy spin columns in 2 ml collection tubes, 1 per RNA sample 2 ml collection tubes from RNeasy kit, 1 per RNA sample 1.5 ml collection tubes from RNeasy kit, 1 per RNA sample 650 μl Rnase free presiliconized tubes for storage of RNA aliquots in $dH_20$/EDTA, 5 per RNA sample screw-cap microfuge tubes for storage of RNA in Et-OH, 1 per RNA sample Label container for storage of samples at −80° C.

3) Add 10 μl BME per ml Lysis Buffer RLT from RNeasy kit Lysis Buffer RLT may form precipitate upon storage. Warm to redissolve.

4) Lysis and homogenmization of cells: (RNeasy step 1b and 2) Remove cell pellets from −80° C. (See Harvesting cells from alginate beads)

Immediately add 600 μl RLT buffer+BME (step 4) directly to each cell pellet; allowing cells to thaw without first adding lysis buffer can lead to RNA degradation.

Mix by pipetting and transfer to labelled 1.5 ml microfuge tubes Vortex each tube 30 seconds at high speed Spin in microfuge momentarily Mix briefly with pipet and transfer to QIA shredder Spin at full speed in microfuge for 1 minute. If insoluble materials is visible in lysate (flowthru), microfuge lysate for 3 minutes at full speed and use only the supernatent for remaining steps. This second microfugation has not bee n necessary to date.

5) RNeasy step 3:

Add 1 volume (600 μl) 70% ethanol/DEPC-$dH_20$ per sample and mix by pipetting. This lysate must not be centrifuged.

6) Application of cell lysate to spin column: (RNeasy step 4)

Transfer 600 μl of lysate to RNeasy spin column. Microfuge 15 seconds at 10,000 rpm (~8,000×g). Discard flow-thru. Transfer remaining lysate into the same column and microfuge as above.

7) Purification of RNA in Spin Column: (RNeasy step 5)

Add 700 μl Wash Buffer RW1 into spin column, centrifuge as above and discard flow-thru. According to the trouble-shooting guide (p 23 of Rneasy manual), allowing the column to sit for 5 minutes after addition of RW1 and before centrifuging may reduce DNA contamination 8) Further purification of RNA in Spin Column: (RNeasy step 6 & 7):

Combine 1 volume of Wash Buffer RPE concentrate (RNeasy kit) with 4 volumes of 100% ethanol (RT), unless RPE buffer has already been diluted with ethanol Transfer the spin column used above into a new 2 ml collection tube;

RNA is still in column. Add 500 μl of Wash buffer RPE/Ethanol (1:4) to spin column.

Microfuge as above

Discard flow through

Add 500 μl Wash buffer RPE/Ethanol (1:4) again to same spin column

Microfuge 2 minutes at full speed

Discard flow thru and collect on tube. Inspect for ethanol on outside of spin column and remove with kimwipe if necessary. Residual ethanol may interfere with subsequent steps. Transfer the spin column used above to a 1.5 ml collection tube supplied with kit.

9) Elution of RNA from spin column: (RNeasy step 8)

Carefully add 30 μl DEPC-treated water/0.1 mM EDTA per sample directly to membrane of the spin column, without touching the membrane with the pipet tip but making sure that the entire membrane is wetted Microfuge for 60 seconds at 8.000×g Repeat above elution, using 20 μl DEPC-treated water/0.1 μmM EDTA and using the same spin column and collection tube, to yield an RNA eluate totaling 50 μl Place all samples on ice during Quantitation and aliquoting.

B. Quantitation of RNA by UV absorbance at 260

1) Transfer 3 μl each RNA sample 57 μl DEPC-treated $H_20$ (20-fold dilution)

(2) Read samples against DEPC-treated $H_20$ blank in short (60 μl volume) 1 cm pathlength quartz cuvette (available on 4thflr. 1 MTN RD) at 260 and 280 nm.

RECORD readings

10.D unit @ 260 nm, 1 cm pathlength+40 ug/ml RNA, and translates to 800 μml after accounting for the 20-fold dilution.

This reading would correspond to a total yield of 40 μpg for a 50 μl sample.

My yields have typically ranged from ~8–80 μg from 8 ml alginate cultures, depending on the conditions of culture. However, since I have done these preps, the methods for harvesting cells from alginate have been modified with the intention of improving cell yield (specifically, the g-force during centrifugation of cells after dissolving alginate beads has been increased ~5-fold).

$A_{260}/A_{280}$+1.7 to 2.0 indicates "highly pure" RNA, 2.0 is ideal. Lower ratios indicate the presence of protein contamination. Typically, the ratio is near 2.0. Readings at 320 nm indicate presence of carbohydrate.

C. Aliquoting

1) For RNA concentrations above 500 μl/ml, dilute to 500 μg/ml by adding DEPC-$dH_20$/0.1 mM EDTA. Record final concentration.

2) For each RNA sample, calculate the volume that is equivalent to 1.0 μg.

3) Make 5 aliquots of 1.0 μg each into 650 μl presiliconized, Rnase-free microfuge tubes.

4) Transfer remaining RNA, if any, to screwtop Rnase-free 1.5 ml microfuge tubes, add 1/10th volume 1% SDS and ≧2.5 volumes 100%

Et-OH, vortex, and store at −80° C.

5) Record all aliquot volumes and concentrations

6) Store all aliquots at −80° C.

Notes i) 1.0 μg RNA aliquots in DEPC-dH20/0.1 mM EDTA: For visualization of RNA on agarose gels or for Rnase Protection Assays, 1.0 μg or less RNA is adequate. Because of the volume of the aliquots may be small (as little as 2 μl) and because of possible dessication of samples in freezer, do not subaliquot the 1.5 μg aliquots stored in aqueous solution until they have been diluted into larger volumes after thawing. Use the 1.0 μg aliquots once and discard any unused RNA after thawing. According to the RNeasy Handbook, RNA stored in water at −80° C., or even −20° C., should be stable for at least a year.

ii) Remaining RNA stored in Ethanol: The samples stored in Ethanol should allow longer-term stability. This RNA must be treated as a suspension, not a solution. Before taking any sub-aliquots from these suspensions, they must be thoroughly vortexed.

Ideally, it is better to precipitate the RNA, remove the ethanol, redissolve in aqueous solution, and requantitate before using.

STOP POINT

D. Visualization of RNA samples on agarose gels (evaluation of RNA degradation)

Materials

Agarose, Molecular Biology Grade (SeaKem GTG), 0.4 g per gel, 14 samples per gel 37% formalin, Autoclaved $dH_20$, ~250 ml per gel

10× MOPS,

Components 0.2M MOPS 50 mM sodiumacetate 10 mM EDTA

DEPC-H20/0.1 mM EDTA

Vacuum dessicator

Recipe

Procedures

3) For 1 µg samples which are 8 µl or less (>125 µg/ml), Combine 1 µl Ethidium bromide per 18 µl 1×RNA Loading Buffer, and add 1×RNA Loading Buffer/EtBr mixture to a final volume of 24 µl.

For all other samples, precipitate (see next step).

4) For 1 µg samples that are more than 4 µl, it is necessary to concentrate samples by ethanol precipitation:

i) To each RNA sample, dilute to final volume of 18 µl with DEPC-H20/0.1 mM EDTA ii) Add 2 µl 3 M Na Acetate, vortex, and add 50 µl 100% Et-OH to each sample.

iii) Vortex again and microfuge at full speed, RT, for 15 minutes. Be sure to orient tube such that you know where the RNA pellet will be.

iv) Aspirate Sup with long pipet tip, avoiding pellet. Microfuge 30 seconds full speed to collect residual ethanol, aspirate sup, and dry for 4' in vacuum dessicator.

v) Combine 1 µl Ethidium bromide per 23 µl 1×RNA Loading Buffer, and add 24 µl to each pellet 5) RNA Ladder: Make one 2 µl aliquot of RNA Ladder for each gel to be run and add 10 µl 1×RNA Loading Buffer 6) Heat all of the RNA samples, including RNA Ladder at 65° C. for 1 minute in heating block, vortex at setting 4–5 for 20 seconds, microfuge momentarily if sample splashes onto side of tube, heat at 65° C. for 15 minutes, and snap cool on ice.

Gel Electrophoresis 8) ufuge momentarily, and load 12 µl of each sample per well, loading RNA Ladder into one well per gel. The quantity loaded will be 0.5 µg per well except the RNA ladder which will be 2 µg per well (~0.33 µg/band). Freeze remainder of samples in case samples need to be rerun.

9) Run gel:

100 Volts, ~85 mA

Run~1 hr (run until bromophenol blue runs~⅔ of gel distance)

10) Photo gel on UV box using photobox apparatus with shield (⅛ second, f-stop=4.5)

Save photo for notebook. The 18S and 28S rRNAs should be clearly visible. Obvious downward smearing of the rRNA bands is indicative of RNA degradation. The intensity of the bands should be comparable among samples, if quantitation and aliquoting were done properly.

STOP POINT

IV RNase protection assays (1–5 days)

A. Preparation of specific cDNAs templates with T7 promoter in antisense orientation:

Prancois Binette, using PCR technology, has synthesized all the human cDNA template used in these studies, with the exception of the 18S rRNA gene which is supplied by Ambion. These cDNAs are linked to ~20 bp of the T7 phage promoter oriented to promote synthesis of radioactive RNA from the human genes in the antisense orientation upon addition of T7 RNA polymerase and radioactive nucleoside triphosphates. Francois' maps of the human genes showing the probe positions and sizes are attached.

The human cDNA templates currently available for these experiments include portions of the genes for:

Collagen Type I: chondrocyte dedifferentiation marker

Aggrecan, Collagen Types II & IX: chondrocyte differentiation markers

Collage Type X: chondrocyte hypertrophy marker

Day 1

B. In vitro transcription from cDNA to prepare antisense radioactive RNA probes from cDNAs, followed by Dnase treatment to remove cDNA template.

should be done within 3 days of Hybridization step, preferably the day before

See MAXIscript™ (Ambion) Instruction Manual for additional information on background, kit components, additional procedures, and troubleshooting.

The Rnase Protection Assay can be done using several probes combined, as long as the probes are different enough in size to allow separation during electrophoresis. However, each probe must be transcribed in separate tubes and gel purified from different lanes of the gel before combining for the Rnase protection assay. In addition to preparing probes from the templates listed above, the 18S rRNA template should also be transcribed for every Rnase protection assay.

Presumably, the quantity of 18S rRNA is equivalent among cells, independent of growth conditions, and is therefore a standard for comparing the amount of total cellular RNA used in the Rnase Protection Assays. Size marker RNA should also be used in each RNase Protection Assay. Unlike the other probes, these can be transcribed as much as 2 months in advance of use and do not need to be gel-purified.

Materials, quantity per probe

From MAXIscript™ T7 (Ambion, Cat #1314) in vitro transcription kit (FOR KITS RECEIVED AFTER Nov. 1, 1995):

10×transcription buffer, 2 μl

ATP solution, 10 mM, 1 μl

GTP solution, 10 mM, 1 μl

UTP solution, 10 mM, 1 μl

T7 RNA polymerase (5 U/μl)+RNase Inhibitor (5 U/μl), 2 μl

DNase I (RNase free), 2 U/μl, 1 μl

2×Gel Loading buffer, 22 μl:

CTP solution from Ambion MAXIscript kit diluted to 0.05 mM, 3 μl [alpha-32P]-CTP, 3000 Ci/mmole, 10 mCi/ml, 5 μl (only 1 μl for transcription of size markers) This should be ordered for delivery within 3 days of use (Delivery dates are Monday and Friday).

pT-7-Human cDNA templates (from 100 μl PCR rxn performed by FB), 5 μl(~0.5–1.0 μg) each pT7 18S rRNA antisense control template, 0.5 μg/μl (Ambion Cat # 7338) ("R"), 2 μl total pT7 RNA size marker template, 1 μl (unless transcribed within the last 2 months) DEPC-treated $H_20$, up to 13 μl RNase-free, screw-top 1.5 ml tubes, labeled for each probe, 1 Heating blocks for 1.5 ml tubes, one at 37° C. and one at 95° C. Plexiglass radiation shield Procedures 1) Set one heating block to 37° C. and the other to 95° C.

2) Move [alpha-32P]-CTP from freezer to RT

3) Thaw all reagents in table below to RT, except Polymerase and DNase I

4) Briefly vortex and microfuge xcription buffer and XTP solutions

5) To RNase-free 1.5 ml tubes, add components in order shown below (#'s represent ul)

All components, except the templates and polymerase can be combined as one batch, then distributed as 13 μl aliquots, one to each tube to receive template. Then add one template per tube, then polymerase All procedures beginning with the addition of 32 P-CTP must be done using a plexiglass radiation shield Combine components at RT, NOT on ice

| Component(see above) | μl/probe |
|---|---|
| 10X xscription buffer (kit) | 2 |
| ATP (kit) | 1 |
| GTP (kit) | 1 |
| UTP (kit) | 1 |
| CTP (diluted from kit, FB) | 3(for transcription of size marker, use 1 μl of undiluted CTP) |
| $^{32}$P-CTP | 5(for transcription of size marker, use 1 μl) |
| Human cDNA templates | 5 each |
| 18S rRNA gene template | 2 μl template + 3 μl DEPC-$H_2O$ |

-continued

| Component(see above) | μl/probe |
|---|---|
| *Size marker template | 1 μl template + 10 μl DEPC-$H_2O$ |
| T7 RNA Polymerase (kit) | 2 |

After adding polymerase, mix components by pipetting

*Size marker does not need to be transcribed if some has already been prepared in the last 2 months and is still available. There is no need to gel purify size markers after the in vitro transcription reaction.

6) Incubate in 37° C. heating block for 30–60 minutes

During this period, prepare 4% acrylamide gel (See section C below)

7) Add 1 μl of DNase (kit) to each reaction, mix by pipetting, and incubate 15 minutes at 37° C.

8) Add 21 μl 2×Gel loading buffer (kit) and heat to 95° C. for 2–3 minutes prior to this step, gel should be ready; prolonged heating may lead to formation of aggregates in SDS that are not able to enter the gel during electrophoresis.

leave tubes in heating block for loading gel directly from block.

If size markers were transcribed, they can be frozen at this time; no need for gel purification.

C. Gel purification of radioactive probes

Materials

Marathon Gel Mix 4(premix for 4% acrylamide, 8.3M Urea gel), 15 ml per two gels

Ammonium Persulfate (APS), 10% (prepared within one day), 90 μl

Running buffer; 1×TBE, ~300 ml

Gel pouring apparatus

Comb with 40 μl/well capacity (10 teeth, 0.75 mm thick)

Gel electrophoresis apparatus in radiation room

Fine tip pipetman tips

Electrophoresis power supply in radiation room

Plastic wrap

BIOMAX MR film (Kodak, Cat #895 2855)

RNase-free 1.5 ml tubes, 1 per probe+1 for combined probes

Elution buffer (0.5M Ammonium Acetate, 0.2% SDS, 1 mM EDTA), 300 μl per probe

Clean single-edge razor blade

Scintillation fluid (Optiphase "HiSafe"), 5 ml per probe

Scintillation vials, 1 per probe

Scintillation counter, programmed for counting P32

Procedures

1) Clean and assemble gel pouring apparatus

2) Warm Marathon Gel Mix 4 to RT, add APS, swirl the solution and pour gel using 10 ml pipet 3) Insert comb, clamp, and add more gel solution to be sure gel reaches top of teeth on comb. Gel can sit for hours in gel pouring apparatus before proceeding 4) After gel sets (within 30 minutes), remove plate-gel-backing unit from apparatus and rinse plates with tap distilled water. Remove comb and rinse wells 2–3 times, shaking out water between rinses 5) Install plate-gel-backing in electrophoresis apparatus 6) Add 1×TBE to top reservoir, checking for leaking, and then to bottom reservoir 7) Just before adding samples from in vitro transcription (Section I), rinse wells with buffer in top reservoir, using P1000

8) With samples in 95° C. heating block, load 30 μl of each sample into each well, spacing samples with empty wells 9) Hook up power supply and run gel at 125 V for~1 hr or until fast dye is approx ⅔ down gel. Power may be raised to 200 V to speed electrophoresis 10) Remove plate/gel/backing from electrophoresis apparatus and rinse all components thoroughly with tap water.

11) Remove glass plate, leaving gel attached to backing

12) Wrap gel/backing with plasticwrap and expose x-ray film for 60 seconds, noticing orientation of gel and film (gel precisely in upperleft corner of film; dull side of film should be separated from gel by a single layer of plasticwrap)

13) Develop film, and using film as a guide, mark the location of the four bands containing the respective probes on the gel by adding mark directly to plasticwrap over gel with marking pen. Save film for X-ray film binder 14) With razor, cut out each band of the gel containing probe of interest, peal away plasticwrap, and drop each band into a separate 1.5 ml RNase-free tube of 300 μl Elution buffer 15) Incubate gel in elution buffer for 2.5–3 hrs at 37° C., then microfuge 1 minute at full speed 16) Add 10 ml scintillation fluid to each of four labeled scintillation vials 17) Add 3 μl (1% of total volume) from each elution to separate scintillation vials 18) Count radioactivity in scintillation counter on 32P program; Record CPM 19) Calculate the volume in μl, for each probe, equivalent to 25,000 counts 20) Combine probes into one 1.5 ml RNase-free tube, using above calculations to give total of 25,000 n CPM of each probe, where n equals the number of RNase protection assays (including controls) to be done with the probe mixture. Because the energy from radiation can cause chemical breakdown of the RNA, the probes should be used within the next three days, the sooner the better 21) Return unused individual probes to freezer designated for radioactive materials. Use shielded container.

D. Co-precipitation of cellular RNA with antisense probes should be done the day before hydrization step Materials One 650 μl RNase-free tube labeled "P+" (Control for probe; not to be RNase treated)

One 650 μl RNase-free tube labeled "P−" (Control: RNase-treated probe)

From Hybspeed RPA kit (Ambion):

- Elution buffer from, ~130 μl per sample to be run in Rnase Protection assay
- Yeast RNA from Hybspeed RPA kit (Ambion), 10 μl per sample
- 5M Ammonium Acetate from Hybspeed RPA kit, 0–13 μl per sample Combined radioactive probes from Section C, 25,000 cpm per probe per sample One 1.0 μg aliquot of each cellular RNA sample to be probed (each in 650 μl RNase-free tubes).

- Ideally, this should include an aliquot or aliquots of cellular RNA which are known from previous assays to contain the RNA targeted by the probes being used (positive control) and one aliquot of cellular RNA from fibroblasts known not to express chondrospecific genes (negative control).

Cold 100% Ethanol, 375 μl per sample

Procedures

1) Combine (n+2)10 μl Yeast RNA+(n+2)130 μl Elution buffer in one tube where n=# of samples, including all controls, with volume of less than 10 μl 2) To above mix, add (n+2)y μl of probe mix from section C where n=# of samples, including all controls, with volume of less than 10 μl where y μl=volume of probe mix which contains 25,000 cpm of each probe 3) Add (140+y) μl to:
   - empty tube labeled P+
   - empty tube labeled P−
   - each tub with cellular RNA samples unless volume of RNA sample exceeds 10 μl 4) To each RNA sample with volume exceeding 10 μl, add:
   - $1/10^{th}$ volume of 5M Ammonium Acetate
   - 10 μl of Yeast RNA
   - Enough Elution buffer to bring total volume to 140 μl
   - y μl (see above) of combined probe 5) Briefly vortex samples, add 375 μl (~2.5 volumes) of cold 100% EtOH, and invert ~40×

6) Place all tubes and unused probe in "hot" freezer to allow co-precipitation for 1 hr or o/n Day 2

E. Hybrization of cellular RNA with antisense probes and Rnase treatment to remove ssRNA See HybSpeed™ RPA (Ambion, Cat #1412) Instruction Manual for additional information on background, kit components, additional procedures, and troubleshooting.

Materials

Three Heating blocks for 650 μl tubes, set for 95, 68, & 37° (near radioactive shields)

From HybSpeed RPA kit (Ambion, Cat # 1412):

- Rnase Digestion Buffer, 100 μl per cellular RNA and probe control samples
- Hybridization Buffer, 10 μl per cellular RNA and probe control samples
- Gel Loading Buffer II, 10 μl per cellular RNA and probe control samples, and for size marker
- One lane of size markers should be loaded per gel; one or two gels will be loaded, depending on number of samples (maximum of 10 lanes per gel)
- Rnase A/T1 Mix (enzyme: keep in freezer until use and return to freezer immediately, 1 μl per sample
- Inactive/Precipitation Mix (keep in freezer until use), 150 μl per cellular RNA and probe control samples Co-precipitation tubes containing cellular RNA and probe stored o/n in freezer (Section D)

Mifrofuge in cold room elongated pipetman tips (fine-tip)

vacuum flask designated for radioactive waste radioactive shields (in Laboratory)

1% SDS, several mls for washing pipet tips

70% Ethanol, stored at −20° C., 300 μl per cellular RNA and probe control samples Timer Procedures These Procedures may be performed in the lab (Radiation Room not necessary).

Perform procedures behind plexiglass radioactive shields, and use radioactive waste container.

Pay close attention to incubation times and temperatures.

1) Preheat one heating blocks and waterbath (These should all be in close proximity to each other)

2) Preheat Rnase digestion buffer to 37° C.

3) Thaw Hybridization Buffer and Gel Loading Buffer II to room temperature

4) Pellet RNA precipitate: Remove o/n co-precipitation tubes from freezer (Section D) and microfuge at full speed for 15 minutes in cold room. Orient tubes such that you will know where the pellet is.

5) Using elongated pipetman tips (fine-tip), carefully aspirate supernatent (ethanol) into flask designated for radioactive waste.

Do not touch pellet. Rinse pepetman tip in 1% SDS between each tube.

6) Wash RNA pellet: To each pellet, gently (so as to not dislodge the pellet) add 300 μl cold 70% Ethanol. Invert tubes gently ~4 times, and microfuge at full speed for 5 minutes in cold room.

7) During centrifugation, aliquot the amount of Hybridization Buffer needed and heat to 95° C.

8) Repeat aspiration, removing as much Ethanol as possible from sides of tube without disturbing pellet.

9) Place pellets in 95° C. heat block and add 10 μl of preheated hybridization buffer to each tube.

10) Solubilization: Vortex each sample for a full 20 seconds; return each sample to 95° C. immediately after vortexing (Proceed quickly, vortexing two tubes at a time).

Revortez~10 seconds each, returning each sample to 95° C. immediately.

"Resolubilization of the coprecipitated probe+RNA is essential for maximizing the sensitivity of the HybSpeed System. Do not be concerned by foaming that may occur."

11) Hybridization: After 2–3 minutes at 95° C., transfer tubes quickly to 68° C. waterbath and incubate for 10 minutes.

"Do not allow temperature of samples to drop"

12) During 10 minute hybridization, aliquot remove Rnase A/TI, vortex and microfuge briefly, and dilute 100:1 by adding 1 μl into every 100 μl of Rnase Digestion Buffer (buffer prewarmed to 37° C.). Return stock Rnase to freezer. Briefly vortex and microfuge diluted Rnase. Keep diluted Rnase and unused Digestion Buffer at 37° C. "Do not put on ice". You will need 100 μl Digestion Buffer without Rnase for "P+" sample).

13) Digestion of non-hybridized ssRNA: At the end of the 10 minute hybridization, One tube at a time, transfer sample from 68° C. bath directly to 37° C. block and immediately add 100 μl of diluted Rnase prewarmed to 37° C.

Exception: To tube labeled "P+" (see Section D), do not add diluted Rnase. Instead, add 100 μl of Digestion Buffer without Rnase. This sample will show the migration of intact probes during electrophoresis.

14) After all tubes have been treated as above, vortex each tube briefly and return to 37° C. for 30 minutes, revortexing after the first 15 minutes. During this incubation, you may want to pour gel for electrophoresis (see below).

15) At end of 30' Rnase- treatment, add 150 μl of cold Inactivation/Precipitation Mix to each tube.

Vortex and microfuge briefly. Transfer tubes to −20° C. freezer for at least 15 minutes (Can leave for several hours).

F. Electrophoresis of protected RNA

Pour 1 gel per maximum of 9 samples (not including marker lane)

Materials, per 4% acrylamide/8.3M Urea gel

| From PAGE 1 Sequencing Gel Kit (Boehringer Cat# 100688): | |
|---|---|
| Component 1: Acrylamide:Bisacrylamide (19:1)/8.3 M Urea, | 1.6 ml |
| Component 2: Diluent, 8.3 M Urea, | 7.4 ml |
| 10X TBE/8.3 M Urea (Boehringer Cat# 100919), | 1.0 ml |
| Ammonium Persulfate (APS), 10% (prepared within one day) | 70 μl |
| TEMED | 10 μl |
| Running buffer: 1X TBE, ~300 ml | |
| Gel pouring apparatus | |
| Comb (10 teeth, 0.75 mm thick) | |
| Gel electrophoresis apparatus | |
| Fine tip pipetman tips | |
| Electrophoresis power supply | |
| Plastic wrap | |
| BIOMAX MR Kodak film | |
| Radioactive RNA size markers (transcribed as described in section B) | |
| Samples in Inactivation/Precipitation Mix | |
| Elongated pipetman tips (fine-tip) | |
| Vacuum flask designated for radioactive waste | |
| Gel Loading Buffer II from HybSpeed RPA kit, 10 μl per sample | |
| Heating block for 650 μl tubes set at 90° C. | |

Procedures

1) Pour 4% acrylamide/8.3M Urea gel: follow steps 1–5 of Section C 2) 2)O Thaw radioactive size markers and Gel Loading Buffer 3) Remove samples in Inactivation/Precipitation Mix from freezer and microfuge 15 minutes at maximum speed in cold room 4) During centrifugation, remove plate-gel-backing unit from apparatus and rinse plates with tap distilled water. Remove comb and rinse well 2–3 times, shaking out water between rinses 5) Install plate-gel-backing in electrophoresis apparatus 6) Add 1×TBE to top reservoir checking for leaking, and then to bottom reservoir 7) After 15 minute centrifugation, using elongated pipetman tips (fine-tip), carefully aspirate supernatent (ethanol) into vacuum flask designated for radioactive waste.

Do not touch pellet Rinse Pipetman tip in 1% SDS between each tube.

8) Microfuge 30 seconds full speed in cold room and aspirate again

"Residual supernatent will cause aberrant migration of bands in gel"

9) Add 10 μl Gel Loading Buffer, vortex vigorously and microfuge briefly

10) Heat samples in heating block to 90° C. for 3–4 minutes. Note: heating too long may cause samples to become trapped in well of gel.

11) Just before adding samples, rinse wells with buffer in top reservoir, using P1000

12) With samples in 90° C. heating block, load 8 μl of each sample per wells

Exceptions

Markers: Dilute 1 μl into 9 μl Gel Loading Buffer and load only 1 μl into well. Markers do not need to be heated. As marker decays (half life=2 weeks), increase amount of marker loaded accordingly.

"P+" control probe sample: load only 1 μl

Note on loading: If possible, avoid use of end lanes and leave an empty well between the Marker land and the adjacent sample 13) Hook up power supply and run gel at 125 V until fast dye is near end of gel 14) Remove plate/gel/backing from electrophoresis apparatus and rinse all components thoroughly with tap water.

15) Remove glass plate

16) Transfer gel from backing plate to Wharman paper and dry on gel dryer

G. Phosphoimager

1) Expose gel in erased phosphoimager cassette, recording position of gel on grid 2) After 1–4 days exposure, scan image and quantify bands DNA fragments containing partial sequences of aggregan (Agg) (Doege et al., J. Biol. Chem 266:894–902, 1991) and types I and II collagens (Kuivaniemi et al., Biochem J. 252:633–640, 1988 and Baldwin et al., Biochem J. 262:521–528, 1989) were generated by PCR amplification of human chondrocyte cDNA libraries. Paired oligonucleotides, representing coding sequences within each gene separated by several hundred basepairs (bp) were used as primers for PCR. Included at the 5' end of the downstream primer, was an anchor sequence (CAGTGCCAT) for subsequent addition of the T7 RNA polymerase promoter. The sequence of the primers with upstream and downstream sequences shown respectively in 5' to 3' orientation are as follows:

i) CCATGCAATTTGAGAACT (SEQ ID No:1); and ii) ACAAGAAGAGGACACCGT (SEQ ID No:2) to generate 551 bp of aggregan gene sequence ($Agg_{551}$);

iii) CCATGCAATTTGAGAACT (SEQ ID No:3); and iv) CTTCGATGGTCCTGTCGTTCAG (SEQ ID No:4); for $Agg_{207}$;

v) GCGGAATTCCCCCAGCCACAAAGAGTC (SEQ ID No:5); and vi) CGTCATCGCACAACACCT (SEQ ID No:6) for 261 bp of the type II collagen (CI) gene; and vii) GTCCCCGTGGCCTCCCCG (SEQ ID No:7); and viii) CCACGAGCACCAGCACTT (SEQ ID No:8) for 307 bp of type II collagen gene (CII).

The amplified fragments were inserted into pCRscript vector (Stratagene, Lajolla Calif.) for the propagation and maintenance. In order to generate templates for the transcription of antisense probes, a second PCR amplification was performed using these cloned cDNA fragments. For priming, respective upstream primers shown above were each paired with the T7 promoter sequence containing the same anchor sequence (underlined) that use used in the first PCR amplification:

GGAATTCTTAGATAATACGACTCACTATAGGGCAGTGCCAT (SEQ ID No:9); DNA templates containing either 80 bp of the 18S rRNA gene or 316 bp of the glyceraldehyde-3-phosphate dehydrogenase (GAPDH) gene, each linked to an upstream T7 promoter, were supplied by Ambion (Austin, Tex.). Prior to use as a template, GAPDH sequence linked to the promoter was reduced to 149 bp by digestion with Dde I.

In vitro transcription from the above templates was performed using the Maxiscript™ kit (Ambion) according to manufacturer's instructions. Full-length probes were purified from the transcription reaction by electrophoresis on 7M urea, 4% polyacrylamide 1×TBE gels, followed by autoradiography, excision from the gel of bands corresponding to the full length transcripts, and passive diffusion into probe elution buffer (supplied in the Maxiscript™ kit) for two hours at 37° C. The activity of the probe was quantified by scintillation counting.

RNase protection assays were performed using the Hybspeed™ RPA kit (Ambion) according to manufacturer's instructions. Briefly, radiolabelled antisense RNA probes for aggrecan and types I and II collagens were combined and hybridized with RNA isolated from chondrocytes, using an excess of probe. A probe for 18S rRNA or GAPDH was also included in each hybridization mixture to normalize for total RNA. For negative controls, yeast RNA alone was combined with probes. For positive controls, probes were hybridized to RNA samples know to contain sequences complementary to all four probes. Digestion with an RNaseA/RNase T1 mix was performed to degrade unhybridized RNAs. Hybridized RNAs protected from digestion were resolved by electrophoresis as described above and visualized by autoradiography or by using a Fujifilm BAS-1500 phosphorimager. Bands on the phoshorimage representing types I and II collagen genes were quantified using MacBAS version 2.4 software. Any signal from the corresponding position of the negative control (no chondrocyte RNA) was subtracted.

Cells in alginate culture were grown in the basal medium described above, supplemented as follows:

Culture 1: 1×ITS+

Culture 2: 1×ITS+and 0.2 ng/ml TGF-β1

Culture 3: 1×ITS+and 1.0 ng/ml TGF-β1

Culture 4: 1×ITS+and 5.0 ng/ml TGF-β1

Cells were harvested at 7 and 21 days for RNA isolation. The results of Rnase Protection Assay on RNA from the 7-day cultures showed that in the absence of TGF-β1 (culture 1), there was little or no detectable CII or Agg mRNA while CI mRNA was abundant. With addition of 0.2 ng/ml TGF-β1 (culture 2) there was a clear induction of mRNA abundance for the chondrocyte differentiation markers CII and Agg, while CI abundance was not significantly altered. Addition of higher TFG-β1 concentrations (cultures 3 and 4) showed a dose-dependent increase CII and Agg with no change in CI. Cultures harvested at 21 days yielded similar results. In a separate example we showed that a 100-fold molar excess of a monoclonal neutralizing antibody against TGF-β, when included with the culture supplements listed for culture 3, yielded results similar to that of culture 1. This effectively eliminates the possibility that the differentiating activity was due to a contaminant of the TGF-β1 preparation.

EXAMPLE 8

Culture conditions for cultures 1, 3 and 4 of example 7 were repeated. In parallel cultures, TGF-β2 was used in place of TGF-β1. The results from the TGF-β1 and β2 cultures were similar to the corresponding cultures from Example 7, indicating that TGF-β1 and β2 have similar properties with respect to induction of chondrogenesis in this culture system.

EXAMPLE 9

Chondrocytes embedded in alginate were cultured in basal medium supplemented with ITS+and 1 ng/ml TGF-β2 for 1,2,4,7, and 21 days. As a negative control, cells were cultured for 21 days in basal medium supplemented with ITS+alone. RNA analysis of these cultures showed a general trend of increasing CII and Agg RNA throughout the first seven days (~5-fold increase in aggrecan and ~40-fold increase in CII). At day 21, the abundance of CII and Agg mRNA apparently dropped off, but remained high compared to day 1.

EXAMPLE 10

As shown in appendix C, 1×ITS+is a mixture of several components including 6.25 μg/ml insulin. This example was performed to determine whether, in the above examples, the insulin in ITS+was playing a role in TGF-β mediated induction of CII and Agg. Secondly, if insulin was playing a role, we wanted to see if it can be replaced by IGF-I. The culture condition of culture 3 in example 7 was repeated. In parallel cultures, ITS+media was reproduced with insulin omitted or replaced with 10 ng/ml IGF-I. The results from 7 day cultures showed that in the absence of insulin and IGF-I, 1 ng/ml TGF-β induced neither CII nor Agg expression. However, addition to the culture of 10 ng/ml IGF-I in lieu of 6.25 μg/ml insulin, restored TGF-β1 mediated induction of these chondrogenic markers to levels comparable to that of condition 3 of example 7. This suggests that the IGF receptor, which binds insulin with low affinity (Schmid, 1995), needs to be activated in order for TGF-β mediated chondrogenesis to occur. Furthermore, the use of IGF-I at approximately 600-fold lower concentration than that of insulin substantially reduces the possibility of contaminating factors affecting differentiation.

In a separate example, other components of the ITS+were omitted or substituted. We found that transferrin and selenious acid could be removed without consequence, and that human serum albumin can replace bovine serum albumin.

In conclusion, a complete defined medium, that includes basal medium supplemented with 1 ng/ml TGF-β1 or β2, 10 ng/ml IGF-I, 1 mg/ml human serum albumin, and may further include 5 μg/ml linoleic acid, will induce de-differentiated human chondrocytes to re-express the chondrocyte differentiated markers CII and Agg in suspension cultures.

The invention claimed is:

1. A method for enhancing the rate of re-differentiation of passaged, de-differentiated, human articular chondrocytes, comprising the step of culturing said passaged, de-differentiated chondrocytes in a medium supplemented with TGF-β and a growth factor selected from the group consisting of: IGF and insulin.

2. The method of claim 1, wherein the TGF-β is TGF-β1.

3. The method of claim 1, wherein the TGF-β is TGF-β2.

4. The method of claim 1, wherein the TGF-β is present at 0.2 to 5.0 ng/ml.

5. The method of claim 1, wherein the growth factor is insulin.

6. The method of claim 1, wherein the growth factor is IGF.

7. The method of any one of claims 1–6, wherein the medium is defined.

8. The method of claim 5, wherein the insulin is supplied by ITS.

9. The method of claim 7, wherein the defined medium further comprises human serum albumin.

10. The method of claim 5, wherein the medium is defined and comprises DME, human serum albumin, insulin and TGF-β.

11. A composition comprising passaged, de-differentiated human articular chondrocytes in a medium supplemented with TGF-β and a growth factor selected from the group consisting of: IGF and insulin.

12. The composition of claim 11, wherein the TGF-β is TGF-β1.

13. The composition of claim 12, wherein the TGF-β is TGF-β2.

14. The composition of claim 12, wherein the TGF-β is present at 0.2 to 5.0 ng/ml.

15. The composition of claim 11, wherein the growth factor is insulin.

16. The composition of claim 11, wherein the growth factor is IGF.

17. The composition of any one of claims 11–16, wherein the medium is defined.

18. The composition of claim 14, wherein the insulin is supplied by ITS.

19. The composition of claim 16, wherein the defined medium further comprises human serum albumin.

20. The composition of claim 15, wherein the medium is defined and comprises DME, human serum albumin, insulin and TGF-β.

* * * * *

UNITED STATES PATENT AND TRADEMARK OFFICE

CERTIFICATE OF CORRECTION

PATENT NO. : 6,150,163

DATED : November 21, 2000

INVENTOR(S) : J. McPherson, et al

It is certified that error appears in the above-identified patent and that said Letters Patent is hereby corrected as shown below:

In the abstract, lines 10-11, "tumor growth factor beta (TGF-β)" should read -- transforming growth factor beta (TGF-β) --;

In column 2, line 67, "tumor growth factor beta (TGF-β)" should read -- transforming growth factor beta (TGF-β) -- and In column 11, line 25, before "8-weeks", insert -- At --.

Signed and Sealed this

Twenty-ninth Day of May, 2001

*Attest:*

Nicholas P. Godici

NICHOLAS P. GODICI

*Attesting Officer*

*Acting Director of the United States Patent and Trademark Office*